US006599255B2

(12) United States Patent
Zhang

(10) Patent No.: US 6,599,255 B2
(45) Date of Patent: Jul. 29, 2003

(54) PORTABLE INTELLIGENT STRETCHING DEVICE

(75) Inventor: Li-Qun Zhang, Chicago, IL (US)

(73) Assignee: Rehabilitation Institute of Chicago, Chicago, IL (US)

( * ) Notice: Subject to any disclaimer, the term of this patent is extended or adjusted under 35 U.S.C. 154(b) by 0 days.

(21) Appl. No.: 09/871,434

(22) Filed: May 31, 2001

(65) Prior Publication Data

US 2002/0183655 A1 Dec. 5, 2002

(51) Int. Cl.7 ......................... A61B 5/103; A61B 5/117; A61H 1/00; A61H 1/02; A61H 5/00

(52) U.S. Cl. ....................... 600/587; 600/592; 600/594; 600/595; 601/5; 601/23; 601/26; 601/27; 601/31; 601/32; 601/33

(58) Field of Search ................................ 600/587, 592, 600/594, 595; 601/5, 23, 24, 26, 27, 29, 31, 32, 33, 34, 35, 36

(56) References Cited

U.S. PATENT DOCUMENTS 4,612,919 A * 9/1986 Best ............................ 128/77
4,669,451 A * 6/1987 Blauth et al. ................. 128/25
4,823,807 A 4/1989 Russell et al.
4,848,326 A * 7/1989 Lonardo ...................... 128/80
5,335,674 A * 8/1994 Siegler ....................... 128/782
5,611,764 A * 3/1997 Bonutti et al. .............. 482/124
5,830,160 A 11/1998 Reinkensmeyer
5,843,004 A * 12/1998 Presl et al. ................. 600/595
6,155,993 A 12/2000 Scott

OTHER PUBLICATIONS

Copy of International Search Report for PCT Application No. PCT/US02/17557.

* cited by examiner

*Primary Examiner*—Timothy L. Maust
*Assistant Examiner*—Anuradha Ramana
(74) *Attorney, Agent, or Firm*—Gardner Carton & Douglas

(57) ABSTRACT

A portable intelligent stretching device for use by patients suffering from spastic and contractured joints and limbs. The intelligent stretching device has a motor and a motor shaft for rotating the joint or limb. The variable velocity and stretch distance of the device is determined by a torque sensor on the joint or limb that communicates information to a controller which subsequently instructs the motor as to the variable velocity and stretch distance.

42 Claims, 3 Drawing Sheets

PORTABLE INTELLIGENT STRETCHING DEVICE

FIELD OF THE INVENTION

The present invention relates to a device for stretching limbs and joints. More specifically, to a stretching device that allows precise stretching throughout the joint range of motion including the extreme positions where spasticity and contracture are most significant.

BACKGROUND OF THE INVENTION

Neurological impairments including stroke, spinal cord injury, multiple sclerosis, and cerebral palsy are the leading causes of adult disability, resulting in spasticity and contracture as one of the largest lasting effects in patients. The hypertonus and reflex hyperexcitability disrupt the remaining functional use of muscles, impede motion, and may cause severe pain. Prolonged spasticity may be accompanied by structural changes of muscle fibers and connective tissue, which may result in a reduction in joint range of motion. For example, stroke patients may develop considerable ankle spasticity or contracture and walk with "drop-foot." An ankle-foot orthosis is often used to stabilize the ankle and correct the foot-drop. Though the ankle-foot orthosis helps support the ankle and provides toe clearance during the swing phase of a gait stride, it may force adaptive behavior on the patients by interfering with ankle plantarflexion and alter the need for muscles to contract at the appropriate time and intensity throughout the gait cycle. The latter may have significant adverse effects on the recovery of the patient's motor control capability. Lack of mobilization may also risk development of contracture, changes in connective tissue length and the number of sarcomeres in muscle fibers.

Physical therapy has long been in use as a mode of rehabilitation for treating persons with spastic limbs or contractured joints. Most often people are afflicted with these types of disabilities from strokes, as discussed herein, spinal cord injury, cerebral palsy, or multiple sclerosis, although affliction can be caused through other diseases and traumatic injuries as well.

Typically, a physical therapist uses physical modalities and physical manipulation of a patient's body with the intent of reducing spasticity and contracture, thereby restoring limb and joint function. Unfortunately, the effects may not be long-lasting, partly due to the limited and sometimes infrequent therapy a patient may receive. Furthermore, the manual stretching is laborious and the outcome is dependent on the experience and subjective "end feeling" of the therapists. Patients may try to restore function to the limbs and joints themselves. Unfortunately, most of the time it is difficult for the patient to have controlled movement without the assistance of a therapist. In addition, it may be difficult for a patient with an impaired limb or joint to maintain continuous motion and resistance to the limb for the treatment to be effective. Of large concern for patients who attempt to rehabilitate on their own is the potential for an increase in injuries due to lack of knowledge or from overexcessive rehabilitation.

For both patients and therapists, there is a need for a device that can stretch and mobilize the joint accurately, reliably and effectively. Furthermore, there is a need for a device to reduce spasticity and contracture that is portable and one that patients can conveniently use in the comfort of their own home such that treatment will be more frequent and provide longer-lasting improvement for the patients.

A number of devices have been developed to exercise the joint and reduce joint spasticity and contracture. One example of the prior art, and one that is generally representative of such prior art devices, discloses serial casting which fixes the limb at a corrected position. This method has been used to correct and treat ankle plantar-dorsi-flexion contracture. Dynamic splinting and traction apply a continuous stretch to the joint involved through an adjustable spring mechanism. This continuous passive motion (CPM) device is widely used in clinics and in a patient's home to move the joint within a pre-specified range, to prevent postoperative adhesion and to reduce joint stiffness. However, existing devices like the CPM machine move the limb or joint at a constant speed between two preset joint positions. Because the machine must be set between two preset positions, normally between the flexible part of the joint range of motion, the passive movement does not usually stretch the extreme positions where contracture and spasiticity are most significant. If a CPM machine is set too high, at a higher rate of speed or to stretch where the contracture and spasiticty are most significant, there is an increased potential of risking injury to the joints because the machine operates at a constant velocity without incorporating the resisting torque generated by the soft tissues. Obviously, significant damage can be done to the joint or limb if the CPM is set too aggressively. Therefore, a need exists for a device that can safely stretch the joint to its extreme positions with quantitative control of the resistance torque and stretching velocity. In addition, there is a strong need for quantitative and objective measurements of the impairment and rehabilitation outcome.

What is needed is a limb and joint therapeutic device to stretch a spastic or contractual joint repeatedly to the extreme positions until a pre-specified peak resistance torque is reached with the stretching velocity controlled precisely based on the resistance torque.

What is further needed is a limb and joint therapeutic device that will evaluate changes in the mechanical properties of spastic joints including changes in passive joint range of motion, joint stiffness and viscosity, and energy loss.

SUMMARY OF THE INVENTION

The present invention satisfies the need for a device that can safely stretch the joint to its extreme positions with quantitative control of the resistance torque and stretching velocity. The present invention provides for a limb and joint therapeutic device that changes velocity in relation to the resistance torque throughout the joint range of motion corresponding directly to a patient's spasticity or contracture.

The present invention further satisfies the need for a limb and joint therapeutic device that is small and portable. Furthermore, the device satisfies the need for a stretching device that can stretch and mobilize the limb or joint accurately, reliably and effectively. Finally, the device satisfies the strong need for quantitative and objective measurements of the impairment of the patients' spasticity or contracture while providing a means for reliably detailing the rehabilitation outcome.

According to the embodiments of the present invention, there is a limb and joint therapeutic device for use by both therapists and patients, whether at home or at a clinic. The limb and joint therapeutic device has a limb support, the limb support securing a limb such that the limb is rotatable with respect to a joint. The device has a motor and a motor shaft, the motor and shaft rotating the joint at a variable velocity. A controller communicates with a torque sensor and the motor such that as the resistance torque from the limb increases, the controller communicates to the motor to decrease the variable velocity.

The above advantages, features and aspects of the present invention are readily apparent from the following detailed description, appended claims and accompanying drawings.

DETAILED DESCRIPTION OF THE INVENTION

Figure 1:
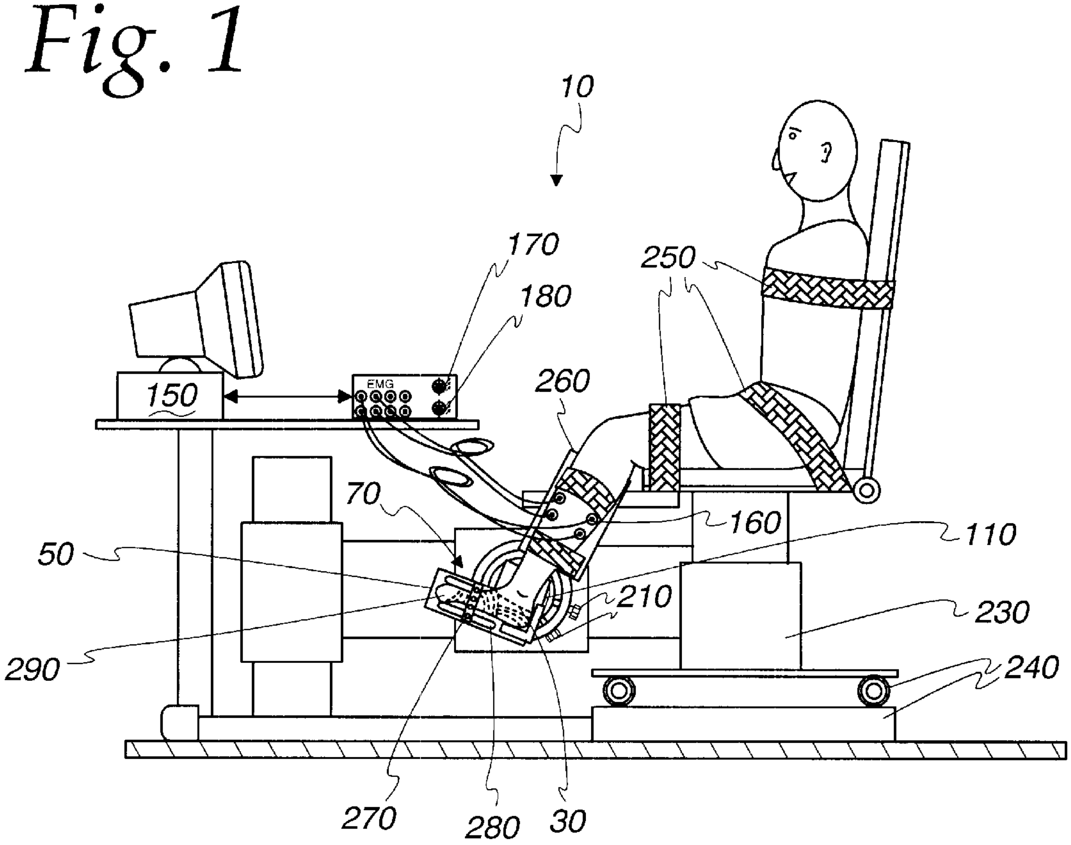
FIG. 1 is a limb and joint therapeutic device for stretching an ankle made in accordance with the principles of the present invention.
Figure 2:
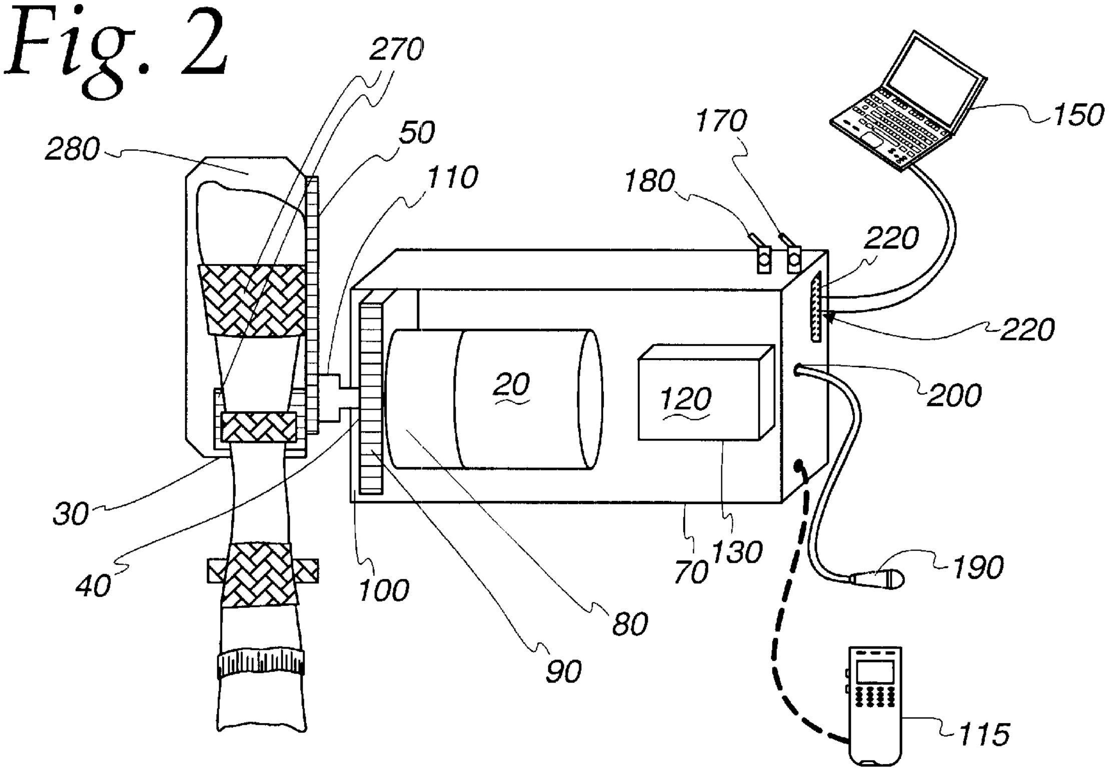
FIG. 2 is the limb and joint therapeutic device for stretching the ankle made in accordance with the principles of the present invention.

Turning first to FIGS. 1–2, there is illustrated, in accordance with a first embodiment of the present invention, a limb and joint therapeutic device 10 having a motor 20 for stretching an ankle 30. The motor 20 has a motor shaft 40 extending in a lateral direction substantially parallel to the axis of rotation of the ankle 30, the motor shaft 40 being mounted to a rotatable side plate 50. The rotatable side plate 50 supports a limb such as a foot and is further secured to a foot plate 280 for resting the patient's foot during use of the device 10. The ankle 30 is then aligned with the motor shaft 40 such that the ankle 30 is rotatable with respect to the motor shaft 40 axis by the motor 20.

The motor 20 is encased within a motor housing 70, the motor housing 70 having an aperture through which the motor shaft 40 extends for rotation of the side plate 50 and the ankle 30. Also encased within the motor housing 70 is a gearhead 80 attached to the motor 20 for reducing speed and increasing the torque output. The gearhead 80 is attached to the motor 20 on one side and is mounted to a mounting frame 90 on the opposing side. The mounting frame 90 is mounted to an inner side 100 of the motor housing 70, the gearhead 80 and the mounting frame 90 having an aperture therethrough such that the motor shaft 40 extends to an outer portion of the motor housing 70. As the motor shaft 40 extends through the motor housing 70, a torque sensor 110 is mounted to the shaft 40 while the shaft 40 is mounted to the rotatable side plate 50. The torque sensor 110 measures the amount of resistance torque and communicates the information to a control box 120.

The motor 20 communicates with the control box 120 which may or may not be provided within the housing 70, the control box 120 having a controller 130. The control box 120 may also have an amplifier 140, the amplifier 140 adapted to communicate with the controller 130 for increasing the amount of electrical current and power to the motor 20 such that velocity may be increased. The controller 130 may be any type of controller 130 including, but not limited to, a digital signal processor, a microprocessor or a microcontroller.

The controller 130 controls the amount of resistance torque as measured by the torque sensor 110, the position of the joint angle and the stretching velocity wherein the controller 130 will be set with a predetermined limit for each prior to the use of the device 10, these limits set by an operator using a computer 150 to communicate with the controller 130 to set the limits. For example, the controller 130 will be set with a maximum resistance torque limit. As this maximum torque limit is achieved, the motor 20 holds the ankle 30 in position for a predetermined amount of time and then reverses the direction of the motor shaft 40 such that the ankle 30 is moved in the opposite direction. In addition, the controller 130 determines the velocity of the movement, the velocity being inversely proportional to the resistance torque such that as the resistance torque increases, the velocity decreases. Conversely, as the resistance decreases, the velocity increases. This inverse relationship is described by the following algorithm:

$$V(t) = \begin{cases} 0, & \text{if } (M_{res}(t) \geq M_p \text{ or } \theta(t) \geq \theta_p + \theta_d) \text{ and need to hold} \\ -V_{\max}, & \text{if } (M_{res}(t) \geq M_p \text{ or } \theta(t) \geq \theta_p + \theta_d) \text{ and have held long enough} \\ \max\left(\frac{C}{M_{res}(t)}, V_{\min}\right), & \text{if } 0 < M_{res}(t) < M_p \\ \min\left(\frac{C}{M_{res}(t)}, -V_{\min}\right), & \text{if } -M_p < M_{res}(t) < 0 \\ V_{\max}, & \text{if } (M_{res}(t) \leq -M_n \text{ or } \theta(t) \leq \theta_n - \theta_d) \text{ and have held long enough} \\ 0, & \text{if } (M_{res}(t) \leq -M_n \text{ or } \theta(t) \leq \theta_n - \theta_d) \text{ and need to hold} \end{cases}$$

where θ(t) and $M_{res}(t)$ are the ankle 30 position and resistance torque at time t, respectively. $M_p$ and $M_n$ are the specified peak resistance torque at the positive and negative ends, respectively, although both are positive numbers. $V_{min}$ and $V_{max}$ are the magnitudes of the minimum and maximum velocity. C is a constant, scaling the $1/M_{res}(t)$ to the appropriate stretching velocity. $\theta_p$ and $\theta_n$ are the specified positive and negative end of the range of motion. $\theta_d$ represents the allowed further rotation beyond the position limits, thus allowing room for improvement in the range of motion. If $\theta_d$ is a very large number, thus allowing the device 10 to move beyond the position limits, or if $\theta_p$ and $\theta_n$ are set outside the range of motion, the stretching control will be dominated by the resistance torque. On the other hand, if $M_p$ and $M_n$ are large, the stretching will be restricted by the position limits. Generally, the stretching reaches the torque limits at both ends of the range of motion with the position limits incorporated into the control scheme as a safety measure and as an optional mode of stretching, thus $\theta_p$ and $\theta_n$ will be set to approximately match the range of motion and $\theta_d$ will be chosen as a positive number. In this manner, the torque limits will be reached while the position limits still restrict excessive ankle 30 movement.

As described herein, during the stretching exercise, the controller 130 controls the stretching velocity according to the resistance torque. In the middle range of motion where resistance is low, the motor 20 will drive the motor shaft 40, and stretch the relatively slack muscles quickly at higher rates of speed. Near the end of the range of motion, the gradually increased resistance torque is measured by the controller 130 such that the controller 130 will then slow the motor 20 and subsequently the motor shaft 40 so that the muscle-tendons involved will consequently be stretched slowly. The result is a greater ankle 30 range of motion. Upon reaching the specified peak of resistance torque, the motor 20 will hold the joint at the extreme position for a period of time, which may range from about a few seconds to several minutes as will be appreciated by one skilled in the art. This improvement over the prior art allows for an increase in the range of motion of the stretch, yet, because of the variability in velocity of the motor 20, minimizes potential ligament and joint damage.

During movement of the limb and joint, the joint angle, resistance torque and Electromyogram (EMG) signals from the soleus, gastronemius and tibialis anterior muscles are recorded. The EMG signals are recorded via electrodes 160 attached to these muscles and subsequently connected to the computer 150 for recordation and further analysis. The electrodes 160 emit electronic signals to the computer 150 corresponding to those emitted by the muscles. The computer 150 can then communicate with the controller 130 to increase or decrease the limits of the range of motion or the variable velocity based upon the information provided by the electrodes 160 to better tailor the device 10 to a specific patient.

The preferred embodiment of the present invention has a number of built-in safety functions. An operator will enter the maximum amount of resistance torque and a position limit, the position limit indicating the maximum and minimum angular position of the ankle 30 during rotation such that the ankle 30 is stretched to extreme positions without causing further damage to the joint or limb. If the maximum resistance torque and/or position limits are reached, a torque limit light emitting diode (LED) 170 and position limit light emitting diode 180 positioned on the motor housing 70 will be illuminated. The LED indicators 170, 180 signal the operator that the maximum ranges have been achieved. The controller 130 continually monitors the joint position and resistance torque levels at a speed of approximately 2000 Hz, but speeds above or below that level may also be used as will be appreciated by one skilled in the art. If the controller 130 finds that either the position limit or resistance torque limit are out of their pre-specified range, the controller 130 may be enabled such that the device 10 is automatically shut off, thus preventing injury. Furthermore, at least one stop switch 190 will be provided such that an operator or patient may shut off the device 10 immediately. The stop switch 190 provides a back-up mechanism to shut off the device 10 if either the position limit, resistance torque limit or velocity are out of their pre-specified ranges. It further provides for automatic shutdown by the operator or patient at any time during use of the device 10 should the patient experience any pain or discomfort or for any other reason. The stop switch 190 is connected to the controller 130 through a hole 200 in the motor housing 70 for shutting off the device 10. The operator can also include a certain amount of further rotation beyond the position and resistance torque limits to provide room for improvement in the range of motion of the patient's ankle 30.

Further provided in the preferred embodiment are stopping screws 210 attached to the rotatable side plate 50 supporting the limb. As the rotatable side plate 50 rotates with respect to the motor shaft 40, the screws 210 provide an additional safety mechanism such that as the rotatable side plate 50 reaches the screw 210, the screw 210 stops the side plate 50 from further rotation. The stopping screws 210 are removable and the position of the screws 210 along the side plate 50 may be varied to provide for a greater or lesser range of motion, the range of motion dependent on the patient's individual needs.

The motor housing 70 also has provided a computer interface 220, the computer interface 220 for communication between the controller 130 and a computer 150. The controller 130 communicates information to the computer 150 for further data analysis. The information sent from the controller 130 to the computer 150 includes the joint angle or position or both, the resistance torque and the velocity of the device 10 or any combination of two or more of these including, but not limited to other joint or limb information as well.

The device 10 has an adjustable seat 230 movable along an adjustable track 240 for positioning of a patient. The adjustable seat 230 is movable in both a lateral and a longitudinal direction for aligning the ankle 30 with the motor shaft 40 of the motor 20. The device 10 has a plurality of straps 250 or seat-belts for securing the patient to the seat 230 once alignment of the ankle 30 and the motor shaft 40 has been achieved.

Attached to the adjustable seat 230 is a leg support 260 for stabilizing the leg. Further attached to the leg support 260 and adjustable seat 230 is the rotatable side plate 50 for stabilizing the foot. The seat 230 and leg support 260 are adjustable in multiple degrees of freedom to align the ankle 30 with the motor shaft 40. As additional support for the foot, there is provided a foot clamp 270 for securing the foot against the side plate 50 once the ankle 30 has been aligned with the motor shaft 40. A foot plate 280 is mounted to the side plate 50 for added stabilization of the foot. The foot plate 280 may be adjustable relative to the side plate in the toe-heal, medio-lateral or dorsi-plantar positions, as well as other positions as will be appreciated by one skilled in the art, to achieve the appropriate alignment and stabilization of the ankle 30. Once the adjustment has been completed, the seat 230 and leg support 260 will be secured into the selected position. A cast 290 may be used to enclose the foot, heel and leg for further stabilization of the limb yet allowing movement of the joint. It will be understood by those skilled in the art that movement during the stretching of the ankle 30 could result in further damage and significant pain to the patient, therefore the ankle 30 must be aligned with the motor shaft 40 and the leg must be secured to the leg support 260 such that the leg is immobilized, while the foot is stabilized and only rotational with respect to the ankle 30.

Figure 6:
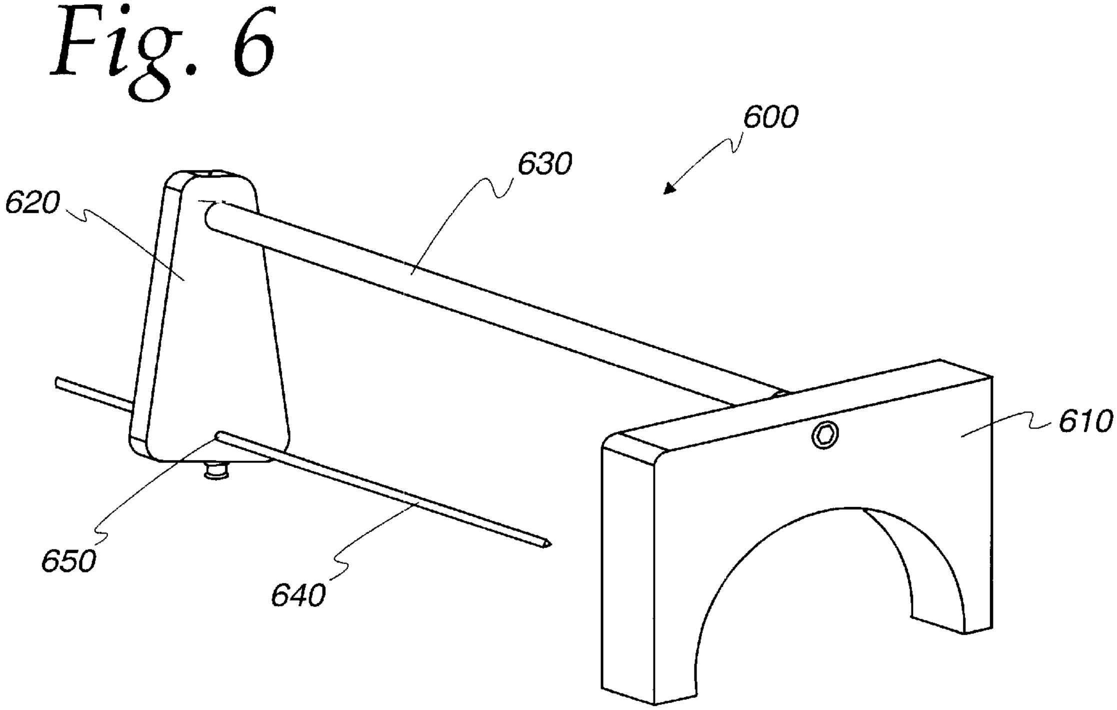
FIG. 6 is an alignment pointer for aligning a joint with a motor shaft made in accordance with the principles of the present invention.

As an additional safety feature for aligning the joint, there is provided an alignment pointer 600 as illustrated in FIG. 6. The pointer 600 has an arc 610, the arc 610 for aligning the pointer 600 with an outer surface of the torque sensor 110. The pointer 600 also has a block 620, the block 620 substantially parallel to the plane of the arc 610, the arc 610 and block 620 secured to one another at a top end by a pole 630. The pointer 600 has a pointer pin 640, the pointer pin 640 slidable through on aperture 650 in a bottom end of said block 620 and extending substantially parallel to the pole 630 and along the same axis as the motor shaft 40 such that the pointer extends toward the center of the torque sensor 110, the pointer pin 640 aligning the joint with the motor shaft thereby preventing injury.

In the preferred embodiment of the present invention, the patient will sit upright in the seat 230 with the knee flexed at about a 60 degree angle as measured between an upper and lower part of the leg. The ankle joint will be manually rotated back and forth several times to check the alignment between the ankle axis and the motor shaft 40. After adjusting the alignment, the limb and joint therapeutic device 10 will be rotated manually by the operator or patient to the ends of the ankle 30 range of motion, thus setting the two extreme positions or, alternatively, the extreme positions may be entered into the computer 150 and subsequently communicated to the controller 130. Once these values have been set, the stretching device 10 will rotate the ankle 30 about its axis throughout its range of motion, the controller 130 controlling the stretching velocity based on the resistance torque via the motor 20 and motor shaft 40.

As discussed herein and embodied in the present invention, EMG electrodes 160 may be attached to the patient's leg to provide specific muscular information to the computer 150. The computer 150 can then analyze the data to show increases in the range of motion, muscular activity and provide recommendations for future stretching. The computer 150 will evaluate changes in the intrinsic properties of contractured and spastic ankles 30 of neurologically impaired patients, including, but not limited to changes in the passive range of motion, joint stiffness, joint viscous damping, energy loss or any combination of those or other intrinsic properties.

One example of the motor 20 used in the present embodiment is an Industrial Drives Goldline B806 servomotor, although other motors 20 may be utilized. The controller 130 controls the velocity and the range of motion of the motor shaft 40. Texas Instruments' TMS320 digital signal processor (DSP) is an example of a type of controller 130 which may be used. As can be appreciated by one skilled in the art, any known controller 130 can be used to control the motor 20.

In an alternate embodiment of the present invention, the torque sensor 110 may be eliminated. This is accomplished by measuring the motor 20 current wherein the current has an approximate linear relationship with the motor torque. This enables the device 10 to be more portable, lightweight and less expensive. In this embodiment, a gearhead 80 may be used with the motor 20 to reduce speed and increase the torque output as necessary. A separate computer 150 is not required as the motor 20 may be controlled by a stand-alone controller 130 or a portable computer or hand-held device 115 having a controller 130, which also aids in reducing the size and expense of the present invention. Electric stops or limits within the motor 20 may be provided as an additional safety mechanism as described herein and known by those skilled in the art.

In the preferred embodiment of the present invention, the controller 130 will monitor the joint position and torque signals at least 2000 times per second and will shutdown the system if either one of these signals are out of the prespecified ranges. Mechanical and electrical stops may be used to restrict the motor range of motion. Both the evaluator and the patient may each hold a stop switch 190 attached to the motor 20, providing a mechanism by which either the evaluator or the patient may shut down the motor 20 by pressing the switch 190.

Figure 3:
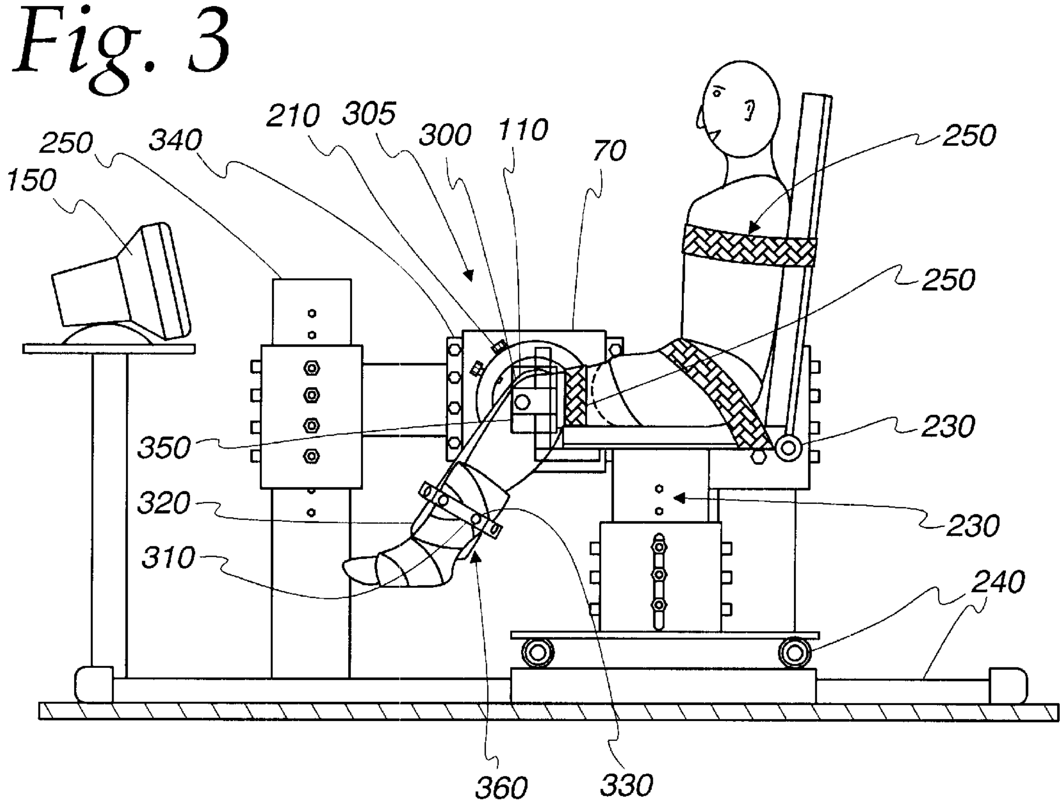
FIG. 3 is a is a limb and joint therapeutic device for stretching a knee made in accordance with the principles of the present invention.

In an alternate embodiment of the present invention as described in FIG. 3, there is provided a limb and joint therapeutic device 305 for stretching a knee 300. Like the first embodiment, the second embodiment includes a height adjustable seat 230 and adjustment tracks 240 for aligning the knee 300 with the motor shaft 40 of a motor 20. Seat belts 250 and straps are provided for immobilizing the patient and an upper portion of the patient's leg once the knee 300 has been aligned. Further provided is a knee clamp 350 for securing the knee 300 to the leg support 360, the leg support 360 having a beam 320, preferably made of aluminum, extending from the knee 300 to the ankle 30 and mounted to the motor shaft 40 and torque sensor 110 such that the knee 300 is only rotatable with respect to the motor shaft 40. Also provided herein are a pair of half rings 310. The half rings 310 secure a lower part of the leg to the leg support 360 having the beam 320 and are secured with tightening screws 330. The tightening screws 330 are adjustable to support various sizes of legs.

In this embodiment of the present invention there is provided a motor housing 70 containing a motor 20, a gearhead 80 and a motor shaft 40, the motor shaft 40 extending through an aperture of the motor housing 70 and through a torque sensor 110. The motor shaft 40 is mounted to the leg support 360 such that as the shaft 40 rotates, the leg support 360 and beam 320 rotate with respect to the knee 300. The motor housing 70 is secured to an adjustable track 250, the housing 70 movable along the adjustable track 250 in a vertical direction for aligning the motor shaft 40 with the knee 300. Like the device 10 for use with the ankle 30 as described herein, the motor 20 communicates with the control box 120 which may or may not be provided within the housing 70, the control box 120 having a controller 130. The control box 120 may also have an amplifier 140, the amplifier 140 adapted to communicate with the controller 130 for increasing the amount of electrical current and power to the motor 20 such that velocity may be increased.

The controller 130 controls the amount of resistance torque, the position of the knee and the stretching velocity and the controller 130 will be set with a predetermined limit for each prior to the use of the device 305 for stretching the knee 300, these limits set by an operator manually or by using the computer 150 to communicate with the controller 130 to set the limits. Like the device 10 for use with an ankle 30, the controller 130 will be set with a maximum resistance torque limit. As this maximum torque limit is achieved, the motor 20 holds the knee 300 in position for a predetermined amount of time and then reverses the direction of the motor shaft 40 such that the knee 300 is moved in the opposite direction. In addition, the controller 130 determines the velocity of the movement, the velocity being inversely proportional to the resistance torque such that as the resistance torque increases, the velocity decreases. Conversely, as the resistance decreases, the velocity increases as determined by the algorithm set forth above.

As described herein, during the stretching exercise, the controller 130 controls the stretching velocity according to the resistance torque. In the middle range of motion where resistance is low, the motor 20 will drive the motor shaft 40, and stretch the relatively slack muscles quickly, at higher rates of speed. Near the end of the range of motion, the gradually increased resistance torque is measured by the controller 130 such that the controller 130 will then slow the motor 20 and subsequently the motor shaft 40 so that the muscle-tendons involved will consequently be stretched slowly. The result is a greater range of motion for the knee 300. Upon reaching the specified peak of resistance torque, the motor 20 will hold the joint at the extreme position for a period of time, which may range from about a few seconds to several minutes as will be appreciated by one skilled in the art. This improvement over the prior art allows for an increase in the range of motion of the stretch, yet, because of the variability in velocity of the motor 20, minimizes potential ligament and joint damage.

During movement of the limb and joint, the joint angle, resistance torque and EMG signals from the leg muscles may be recorded. The EMG signals are recorded via electrodes 160 attached to these muscles and subsequently connected to the computer 150 for recordation and further analysis. The electrodes 160 emit electronic signals to the computer 150 corresponding to those emitted by the muscles. The computer 150 can then communicate with the controller 130 to increase or decrease the range of motion for movement of the knee 300 or the variable velocity based upon the information provided by the electrodes 160 to better tailor the device 305 to a specific patient.

The joint and limb therapeutic device 305 for stretching the knee 300 provides the same safety mechanisms as those for use with an ankle 30. In addition, the device 305 provides a rotation adjustment disk 340 attached to the motor housing 70, the adjustment disk 340 for rotating the motor shaft 40 such that the knee 300 can be aligned with the motor shaft 40. The adjustment disk 340 is further attached to the height adjustment track 245 such that it moves in concert with the motor housing 70 in a vertical direction.

Figure 4:
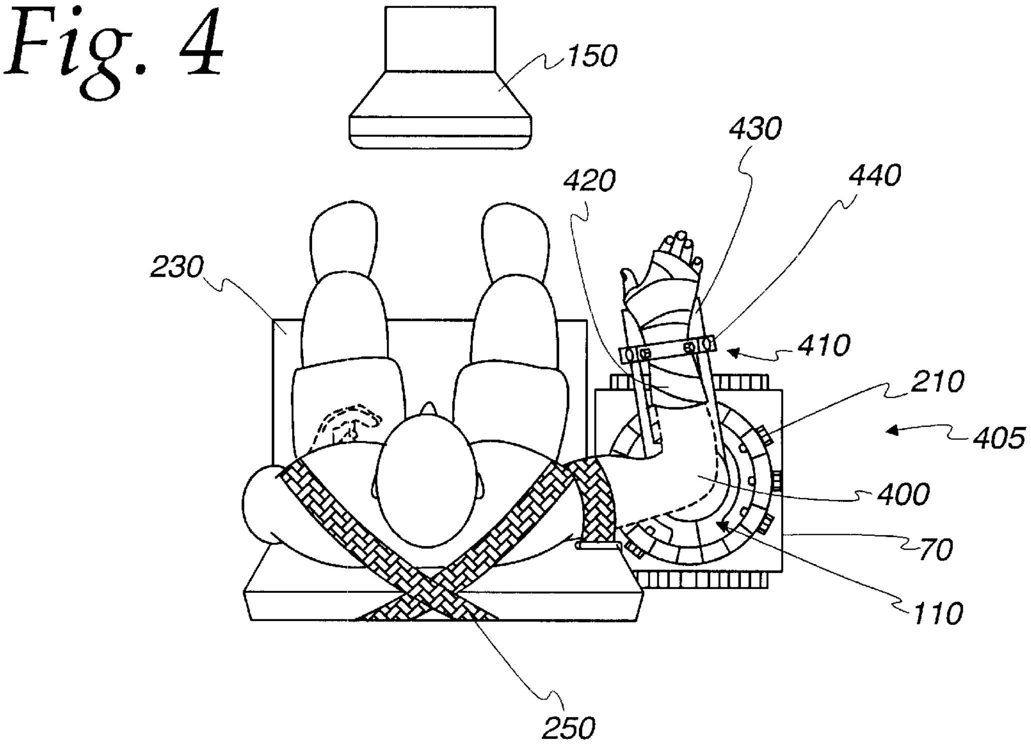
FIG. 4 is a is a limb and joint therapeutic device for stretching an elbow made in accordance with the principles of the present invention.

In an alternate embodiment of the present invention there is provided a joint and limb therapeutic device 405 for use with an elbow 400, as illustrated by FIG. 4, having a motor 20, motor shaft 40 and a gearhead 80 supported within a motor housing 70. The motor housing 70 has an aperture therethrough such that the motor shaft 40 extends in a vertical direction outward of the motor housing 70 and is mounted to a torque sensor 110. The motor shaft 40 and torque sensor 110 are further mounted to an arm support 410, the arm support 410 comprising an aluminum beam 430, although the beam 430 may be made of other materials, the support substantially perpendicular to the motor shaft 40. The arm support 410 therefore holds a lower portion of the arm 420 in substantially a horizontal position. The arm support 410 has a coupling 440 for securing the lower part of the arm to the arm support 410, such that the lower arm is movable only with respect to the elbow 400 and the motor shaft 40. Thus, the motor shaft 40 rotates the elbow 400 at a variable velocity to stretch the joint and therefore improve rotation of the elbow 400.

Similar to the device 305 for use with the knee 300, this embodiment of the present invention includes a height adjustable seat 230 and adjustment tracks 240 for aligning the elbow 400 with the motor shaft 40 of a motor 20. Seat belts 250 and straps are provided for immobilizing the patient and the lower portion of the patient's arm once the elbow 400 has been aligned.

In this embodiment of the present invention the motor housing 70 is secured to a height adjustment track 245, the housing 70 movable along the adjustable track 245 in a vertical direction for aligning the motor shaft 40 with the elbow 400. Like the device 10 for use with the ankle 30 as described herein, the motor 20 communicates with the control box 120 which may or may not be provided within the housing 70, the control box 120 having a controller 130. The control box 120 may also have an amplifier 140, the amplifier 140 adapted to communicate with the controller 130 for increasing the amount of electrical current and power to the motor 20 such that velocity may be increased.

The controller 130 controls the amount of resistance torque, the position of the elbow 400 and the stretching velocity and the controller 130 will be set with a predetermined limit for each prior to the use of the device 405 for stretching the elbow 400, these limits set by an operator manually or by using a computer 150 to communicate with the controller 130 to set the limits. Like the device 10 for use with an ankle 30, the controller 130 will be set with a maximum resistance torque limit. As this maximum torque limit is achieved, the motor 20 holds the elbow 400 in position for a predetermined amount of time and then reverses the direction of the motor shaft 40 such that the elbow 400 is moved in the opposite direction. In addition, the controller 130 determines the velocity of the movement, the velocity being inversely proportional to the resistance torque such that as the resistance torque increases, the velocity decreases. Conversely, as the resistance decreases, the velocity increases as determined by the algorithm set forth above.

As described herein, during the stretching exercise, the controller 130 controls the stretching velocity according to the resistance torque. In the middle range of motion where resistance is low, the motor 20 will drive the motor shaft 40, and stretch the relatively slack muscles quickly, at higher rates of speed. Near the end of the range of motion, the gradually increased resistance torque is measured by the controller 130 such that the controller 130 will then slow the motor 20 and subsequently the motor shaft 40 so that the muscle-tendons involved will consequently be stretched slowly. The result is a greater range of motion for the elbow 400. Upon reaching the specified peak of resistance torque, the motor 20 will hold the joint at the extreme position for a period of time, which may range from about a few seconds to several minutes as will be appreciated by one skilled in the art. This improvement over the prior art allows for an increase in the range of motion of the stretch, yet, because of the variability in velocity of the motor 20, minimizes potential ligament and joint damage.

During movement of the limb and joint, the joint angle, resistance torque and EMG signals from the arm muscles may be recorded. The EMG signals are recorded via electrodes 160 attached to these muscles and subsequently connected to the computer 150 for recordation and further analysis. The electrodes 160 emit electronic signals to the computer 150 corresponding to those emitted by the muscles. The computer 150 can then communicate with the controller 130 to increase or decrease the range of motion for movement of the knee 400 or the variable velocity based upon the information provided by the electrodes 160 to better tailor the device 405 to a specific patient. In addition, the joint and limb therapeutic device 405 for stretching an elbow 400 provides the same safety mechanisms as those for use with an ankle 30 including safety screws 210 and stop switches 190.

Figure 5:
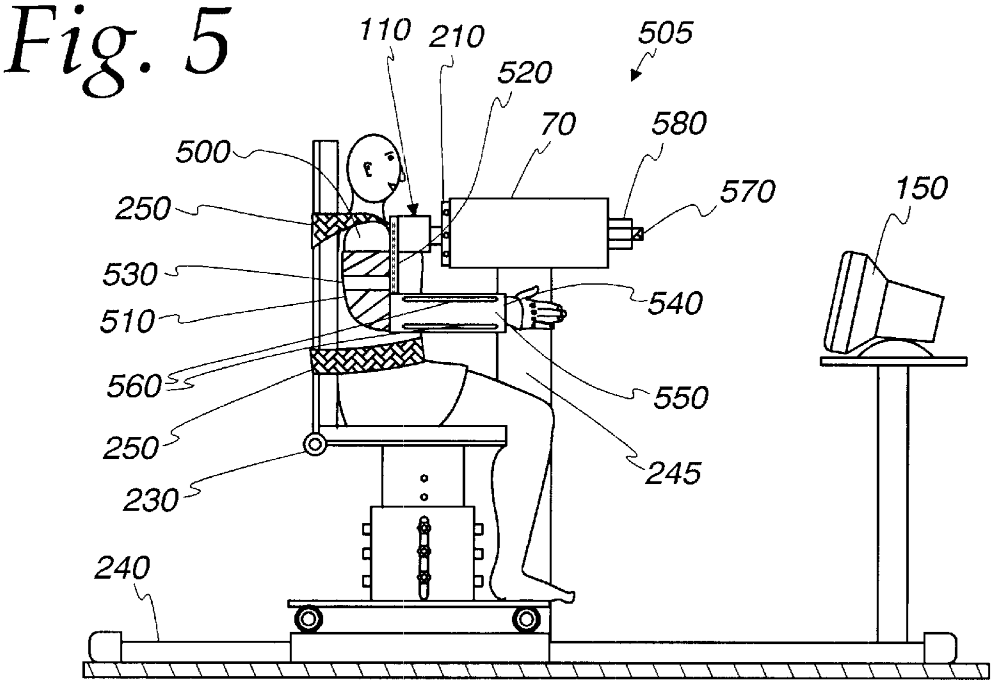
FIG. 5 is a limb and joint therapeutic device for stretching a shoulder made in accordance with the principles of the present invention.

In yet another embodiment of the present invention, there is provided, as shown in FIG. 5, a joint and limb therapeutic device 505 for use with a shoulder 500. In this embodiment, like those for use with other joints, there is provided a motor 20, motor shaft 40 and gearhead 80 encased within a motor housing 70, the motor shaft 40 mounted to a torque sensor 110 and an upper arm 510 support such that the motor shaft 40 rotates the shoulder 500. The upper arm support 510 has an aluminum beam 520 and a ring 530, the ring 530 securing the upper arm to the beam 520, thus forming the upper arm support 510. In addition the upper arm may have a cast for additional immobilization of the upper arm. The upper arm support 510 is further attached to a lower arm support 540. The lower arm support 540 has a pair of arm beams 550 and forearm ring screws 560 securing the lower arm to the lower arm support 540. The upper arm support 510 and lower arm support 540 are mounted to one another such that the arm is movable only with respect to the rotational movement of the shoulder 500 about the motor shaft 40.

The motor housing 70 is mounted to a height adjustment track 245 and is movable in a vertical direction such that the motor shaft 40 can be aligned with the shoulder 500. Furthermore, the device 505 may have an adjustable seat 230 that is movable along an adjustable track 240, such as those discussed herein, for aligning the shoulder with the motor shaft 40. Also provided are position 570 and velocity sensors 580 to provide additional information regarding position and velocity to the controller 130.

Like the other embodiments the controller 130 is connected to a computer 150, the controller 130 communicating with the motor 20, thus controlling the variable velocity, position and resistance torque of the device 505 for stretching a shoulder 500. The controller 130 controls these variables according to the algorithm set forth herein.

While only a few embodiments of the portable intelligent stretching device of the present invention have been described and illustrated in detail herein, it will be evident to one of ordinary skill in the art that other embodiments may be possible for use with a variety of joints and limbs, such as, but not limited to use with fingers and wrists, without departing from the scope of the following claims.

What is claimed is:

1. A portable intelligent stretching device comprising:

a limb support, said limb support securing a limb such that said limb can be rotated at a joint;

a motor having a motor shaft, said motor shaft rotatable at a variable velocity and mounted to said limb support, said joint rotatable with respect to said motor shaft, said joint aligned with said motor shaft;

a torque sensor, said torque sensor positioned between said motor and said limb support, said torque sensor measuring an amount of resistance torque exerted by said joint; and a controller connected to said torque sensor and to said motor, the motor adapted to decrease said velocity as communicated by the controller in response to an increase in resistance torque as communicated to said controller from said torque sensor.

2. The device of claim 1 wherein said joint reaches at least one predetermined torque or position limits, said controller communicates to said motor to reverse the rotational direction of said motor shaft.

3. The device of claim 1 further comprising a torque limit light-emitted diode indicating a maximum allowable amount of resistance torque.

4. The device of claim 1 further comprising a position limit light-emitted diode indicating a maximum and a minimum allowable limb position.

5. The device of claim 1 further comprising a computer, said computer communicating with said controller, said controller providing resistance torque data, velocity data and position data to said computer.

6. The device of claim 1 further comprising an amplifier, said amplifier increasing said variable velocity of said motor.

7. The device of claim 6 further comprising a gearhead mounted to said motor, said gearhead reducing said variable velocity of said motor and increasing the torque output of said motor.

8. The device of claim 7 further comprising a mounting frame, said gearhead and motor fixed to said mounting frame, said mounting frame having an aperture therethrough, said motor shaft extending through said aperture thereby connecting to said limb support.

9. The device of claim 8 further comprising a housing, said housing enclosing said motor, mounting frame, gearhead and amplifier.

10. The device of claim 9 further comprising a height adjustment track for movably adjusting the height of said housing for aligning said motor shaft with said joint.

11. The device of claim 1 further comprising at least one stop switch, said stop switch disconnecting power to said motor wherein rotation of said motor shaft is stopped.

12. The device of claim 1 further comprising Electromyogram sensors connected to a limb of said patient, said Electromyogram sensor transmitting Electromyogram information to said computer.

13. The device of claim 12 wherein said controller communicates with said motor and computer, said computer displaying said Electromyogram information, velocity, position and resistance torque wherein said computer is selected from the group consisting of handheld devices, laptops and desktop computers.

14. The device of claim 1 further comprising a height adjustable seat, said adjustable seat for aligning said motor shaft with said joint.

15. The device of claim 14 further comprising an angular backrest adjustment, said backrest adjustment for further aligning said joint with said motor shaft.

16. The device of claim 14 further comprising seat adjustment position tracks, said tracks positioning said seat proximate or distal said motor shaft further aligning said joint with said motor shaft.

17. The device of claim 16 further comprising a base plate, said base plate securing said adjustment tracks to a surface.

18. The device of claim 1 further comprising a rotation adjustment disk, said disk rotating said shaft for alignment with said limb and having safety screws, said screws limiting the amount of rotation of said motor shaft.

19. The device of claim 1 further comprising at least one safety screw, said at least one safety screw attached to said motor shaft such that said shaft cannot rotate past said at least one screw.

20. The device of claim 1 further comprising at least one clamp and a plurality of screws, said plurality of screws securing said clamp to said limb support for additional stabilization of said limb.

21. A portable intelligent stretching device comprising:

a limb support, said limb support securing a limb such that said limb is rotatable with respect to a joint;

a motor having a motor shaft mounted to said limb support, said joint rotatable with respect to said motor shaft by said motor shaft;

a torque sensor, said torque sensor measuring an amount of resistance torque exerted by said joint; and a computer remotely connected to said motor and said torque sensor, said computer having a controller, said controller controlling the velocity of said motor inversely proportional to the amount of resistance torque measured by said torque sensor.

22. The device of claim 21 wherein said joint reaches at least one predetermined position, said controller communicates to said motor to reverse the rotational direction of said motor shaft.

23. The device of claim 21 further comprising a torque limit light-emitted diode indicating a maximum allowable amount of resistance torque.

24. The device of claim 21 further comprising a position limit light-emitted diode indicating a maximum and a minimum allowable limb position.

25. The device of claim 21 wherein said computer having the controller receives resistance torque data, velocity data and position data.

26. The device of claim 21 further comprising an amplifier, said amplifier increasing said variable velocity of said motor.

27. The device of claim 26 further comprising a gearhead mounted to said motor, said gearhead reducing said variable velocity of said motor and increasing the torque output of said motor.

28. The device of claim 27 further comprising a mounting frame, said gearhead and motor fixed to said mounting frame, said mounting frame having an aperture therethrough, said motor shaft extending through said aperture thereby connecting to said limb support.

29. The device of claim 28 further comprising a base plate, said base plate securing said adjustment tracks to a surface.

30. The device of claim 21 further comprising at least one stop switch, said stop switch disconnecting power to said motor thereby stopping rotation of said motor shaft.

31. The device of claim 21 further comprising Electromyogram sensors connected to a limb of said patient, said Electromyogram sensor transmitting Electromyogram information to said computer.

32. The device of claim 21 wherein said computer is a hand-held device for communicating with said motor.

33. The device of claim 32 further comprising a housing, said housing enclosing said motor, mounting frame, gearhead and amplifier.

34. The device of claim 21 further comprising a height adjustable seat, said adjustable seat for aligning said motor shaft with said joint.

35. The device of claim 34 further comprising an angular backrest adjustment, said backrest adjustment for further aligning said joint with said motor shaft.

36. The device of claim 34 further comprising seat adjustment position tracks, said tracks positioning said seat proximate or distal said motor shaft for further aligning said joint with said motor shaft.

37. The device of claim 21 further comprising a rotation adjustment disk, said disk adjusting the rotation of said shaft.

38. The device of claim 21 further comprising at least one safety screw, said at least one safety screw attached to said motor shaft such that said shaft cannot rotate past said at least one screw.

39. The device of claim 21 further comprising at least one clamp and a plurality of screws, said plurality of screws securing said clamp to said limb support for additional stabilization of said limb.

40. The device of claim 21 further comprising a height adjustment track for movably adjusting the height of said housing for aligning said motor shaft with said joint.

41. The device of claim 21 further comprising an alignment pointer, said pointer aligning said joint with said motor shaft comprising:

an arc, said arc aligned with an outer surface of said torque sensor;

a block, said block parallel to a plane of said arc, said arc and said block secured by a pole at a top end of said arc and said block; and a pointer pin, said pin slidable through a bottom end of said block extending along the same axis as the center of said arc and said torque sensor, such that said pin is on the same axis as said motor shaft.

42. The device of claim 1 further comprising an alignment pointer, said pointer aligning said joint with said motor shaft comprising:

an arc, said arc aligned with an outer surface of said torque sensor;

a block, said block parallel to a plane of said arc, said arc and said block secured by a pole at a top end of said arc and said block; and a pointer pin, said pin slidable through a bottom end of said block extending along the same axis as the center of said arc and said torque sensor, such that said pin is on the same axis as said motor shaft.

* * * * *